(12) United States Patent
Freitag

(10) Patent No.: US 10,478,125 B2
(45) Date of Patent: Nov. 19, 2019

(54) SYSTEMS AND METHODS FOR FLUSHING AN ASSESSMENT CATHETER

(71) Applicant: Pulmonx Corporation, Redwood City, CA (US)

(72) Inventor: Lutz Freitag, Hemer (DE)

(73) Assignee: Pulmonx Corporation, Redwood City, CA (US)

( * ) Notice: Subject to any disclaimer, the term of this patent is extended or adjusted under 35 U.S.C. 154(b) by 273 days.

(21) Appl. No.: 14/195,532

(22) Filed: Mar. 3, 2014

(65) Prior Publication Data

US 2014/0180155 A1 Jun. 26, 2014

Related U.S. Application Data

(63) Continuation-in-part of application No. 13/023,722, filed on Feb. 9, 2011, now abandoned, which is a continuation of application No. PCT/US2009/056392, filed on Sep. 9, 2009.

(60) Provisional application No. 61/774,322, filed on Mar. 7, 2013, provisional application No. 61/095,582, filed on Sep. 9, 2008.

(51) Int. Cl.
*A61B 5/00* (2006.01)
*A61B 5/08* (2006.01)

(52) U.S. Cl.
CPC .............. *A61B 5/6852* (2013.01); *A61B 5/08* (2013.01)

(58) Field of Classification Search
CPC ..... A61M 2025/0019; A61B 2090/701; A61B 90/70; A61B 17/12022; A61B 17/12136; A61B 1/125; B08B 9/0321
See application file for complete search history.

(56) References Cited

U.S. PATENT DOCUMENTS

| | | | | |
|---|---|---|---|---|
| 5,738,824 A | * | 4/1998 | Pfeifer | A61B 1/00057 134/18 |
| 2006/0264772 A1 | | 11/2006 | Aljuri et al. | |
| 2007/0100204 A1 | * | 5/2007 | Feld | A61B 1/00057 600/117 |
| 2007/0142742 A1 | | 6/2007 | Nikolai et al. | |
| 2008/0178880 A1 | * | 7/2008 | Christopher | A61M 16/0051 128/204.23 |
| 2013/0098400 A1 | * | 4/2013 | Nguyen | A61B 1/123 134/18 |

* cited by examiner

*Primary Examiner* — Thomas M McEvoy
(74) *Attorney, Agent, or Firm* — Wilson Sonsini Goodrich & Rosati

(57) ABSTRACT

Devices systems and methods are disclosed for removing secretions from the lumen of a functional assessment catheter for the lungs. The system comprises a flushing unit configured to deliver a clearing fluid to the lumen of the pulmonary catheter to remove debris, secretions, or moisture from the lumen or sensors.

10 Claims, 14 Drawing Sheets

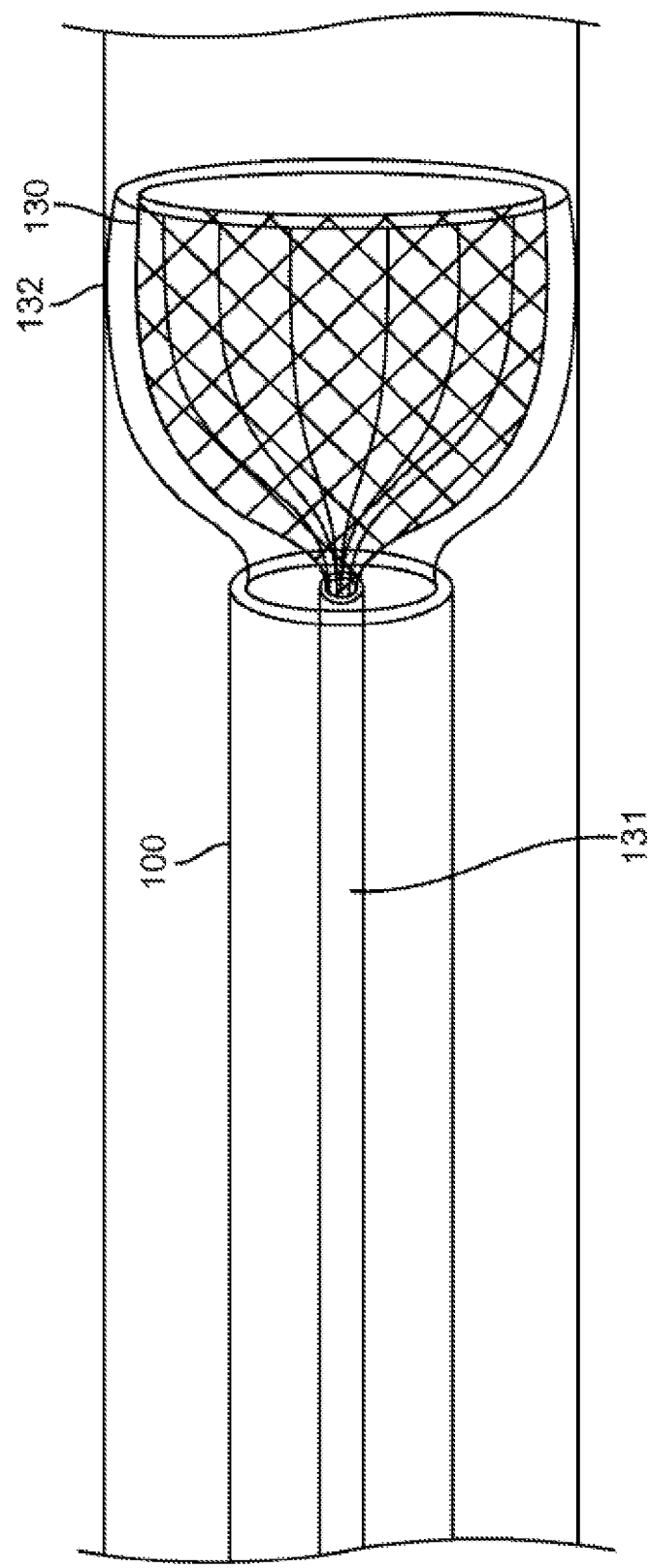

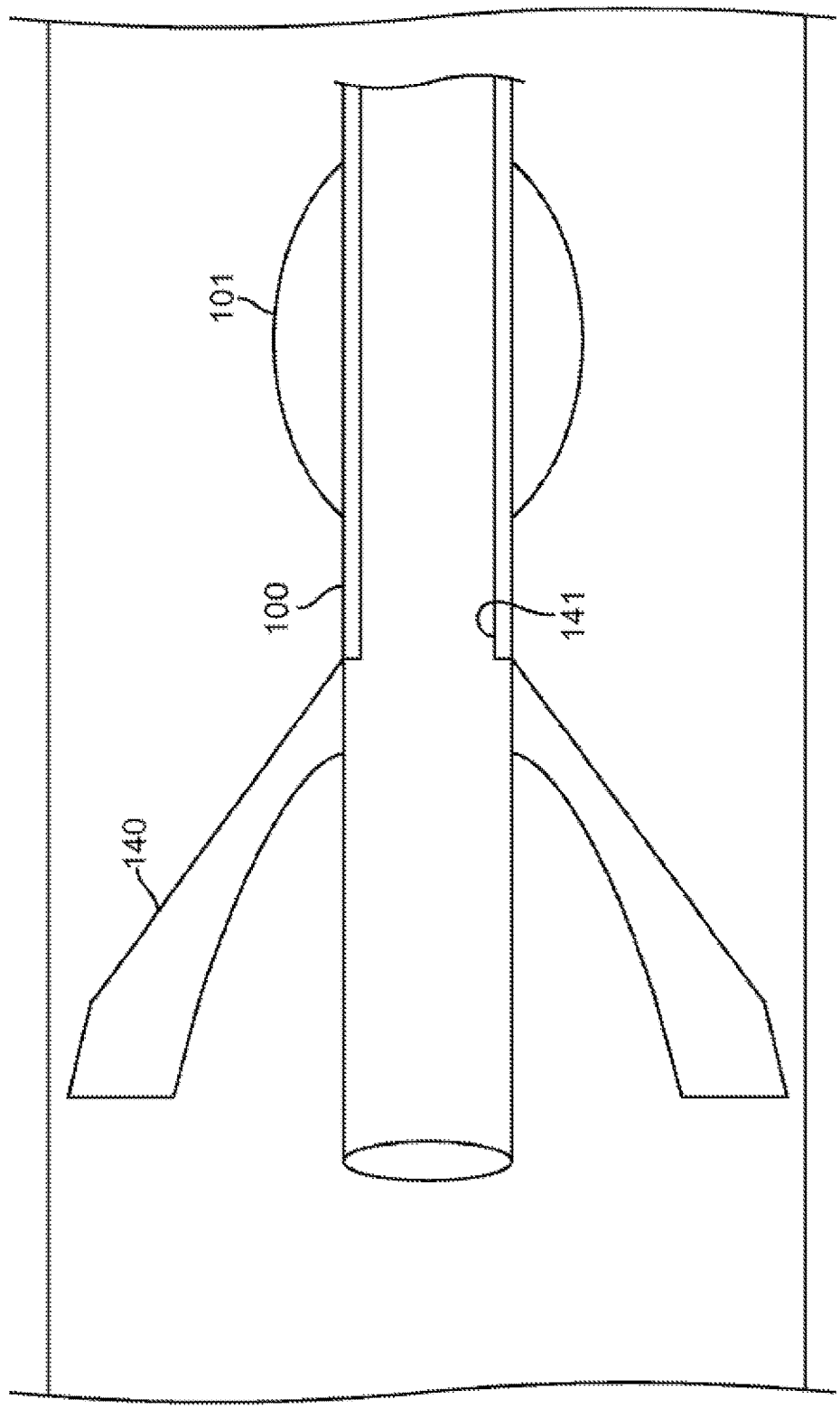

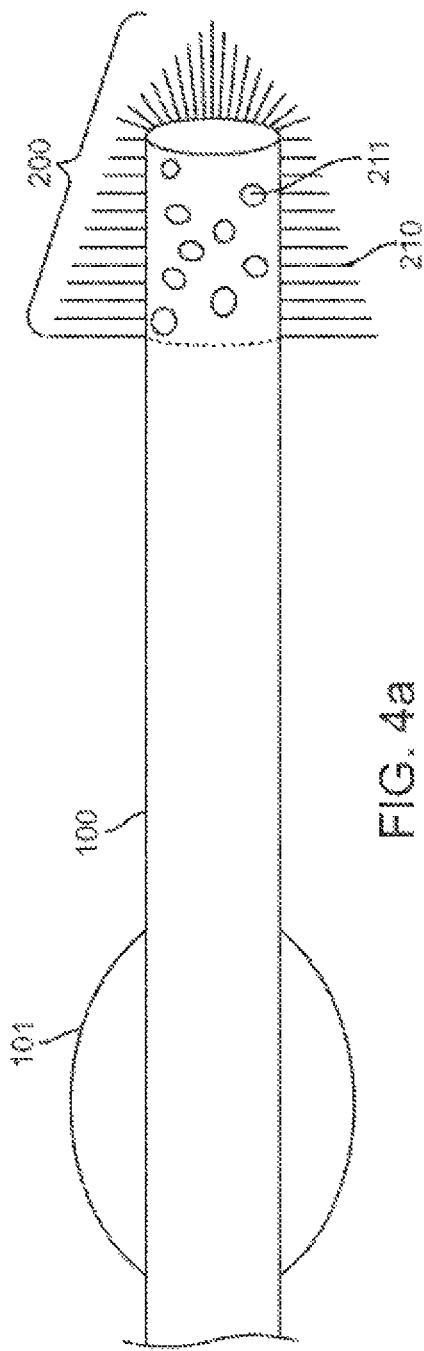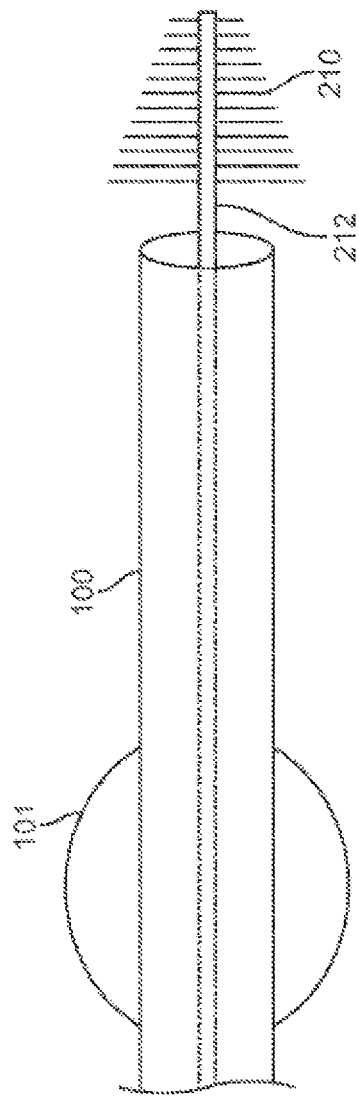

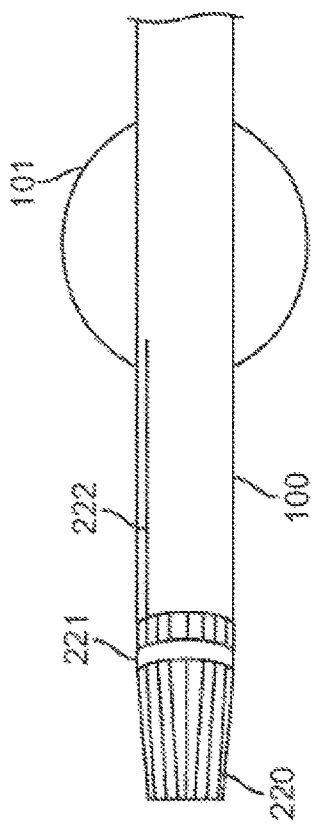
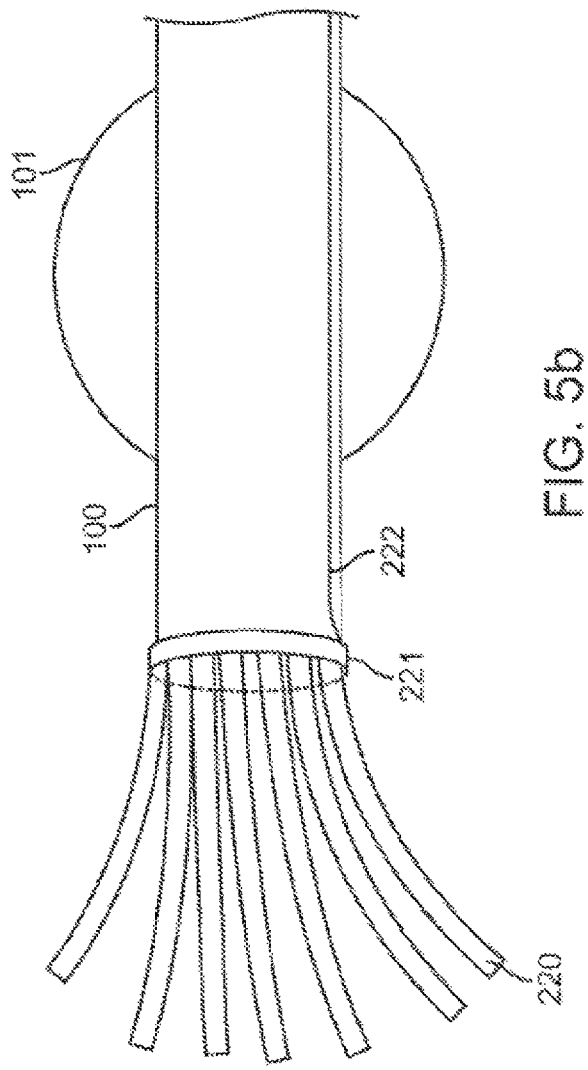

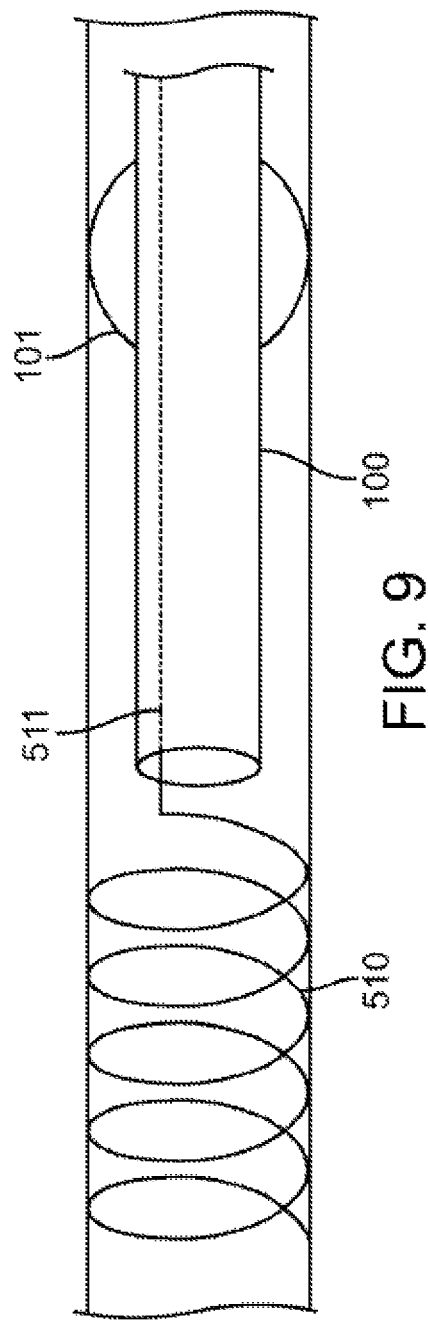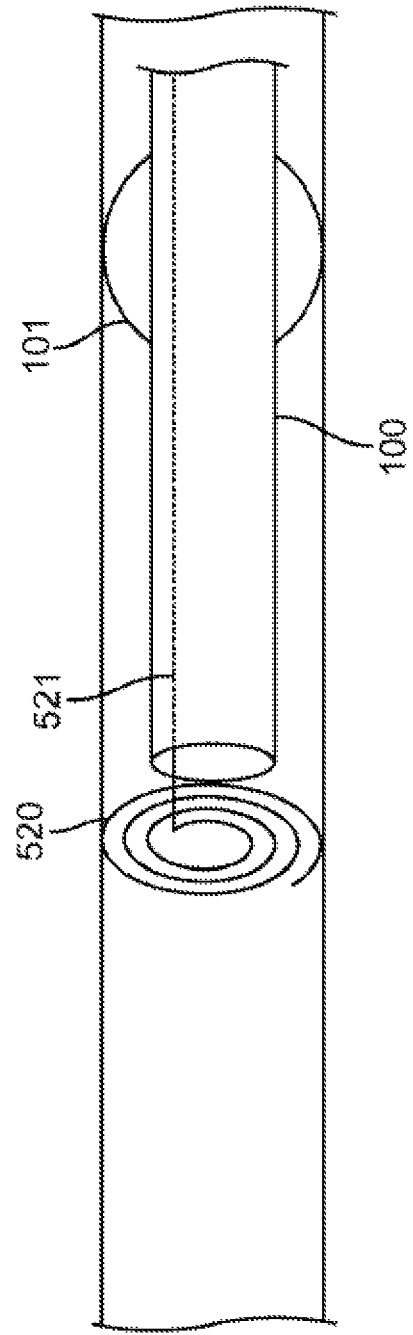

SYSTEMS AND METHODS FOR FLUSHING AN ASSESSMENT CATHETER

CROSS-REFERENCE TO RELATED APPLICATIONS

The present application claims priority to U.S. Provisional Application No. 61/774,322, filed Mar. 7, 2013, the full disclosure of which is incorporated herein by reference. The present application is a continuation-in-part of U.S. patent application Ser. No. 13/023,722, filed Feb. 9, 2011, which is a continuation of International Patent Application No. PCT/US2009/056392, filed Sep. 9, 2009, which claims priority to U.S. Provisional Application No. 61/095,582, filed Sep. 9, 2008, the full disclosures of which are incorporated herein by reference.

BACKGROUND OF THE INVENTION

1. Field of the Invention

This invention relates generally to catheters and more specifically to catheter apparatus and approaches for minimizing entry of secretions or debris into or removal of secretions or debris from the catheter and more particularly in those catheters that are used for assessing pulmonary function.

Chronic obstructive pulmonary disease is a significant medical problem affecting 16 million people or about 6% of the U.S. population. Specific diseases in this group include chronic bronchitis, asthmatic bronchitis, and emphysema. While a number of therapeutic interventions are used and have been proposed, none are completely effective, and chronic obstructive pulmonary disease remains the fourth most common cause of death in the United States. Thus, improved and alternative treatments and therapies would be of significant benefit.

Of particular interest to the present invention, lung function in patients suffering from some forms of chronic obstructive pulmonary disease can be improved by reducing the effective lung volume, typically by resecting diseased portions of the lung. Resection of diseased portions of the lungs both promotes expansion of the non-diseased regions of the lung and decreases the portion of inhaled air which goes into the lungs but is unable to transfer oxygen to the blood. Lung volume reduction is conventionally performed in open chest or thoracoscopic procedures where the lung is resected, typically using stapling devices having integral cutting blades.

While effective in many cases, conventional lung volume reduction surgery (LVRS) is significantly traumatic to the patient, even when thoracoscopic procedures are employed. Such procedures often result in the unintentional removal of healthy lung tissue, and frequently leave perforations or other discontinuities in the lung which result in air leakage from the remaining lung. Even technically successful procedures can cause respiratory failure, pneumonia, and death. In addition, many older or compromised patients are not able to be candidates for these procedures.

As an alternative to LVRS, endobronchial lung volume reduction (ELVR) uses endobronchially introduced devices which plug or otherwise isolate a diseased compartment from healthier regions of the lung in order to achieve volume reduction of the diseased compartment. Isolation devices may be implanted in the main airways feeding the diseased region of the lung, and volume reduction takes place via absorption atelectasis after implantation or via collapse by actively suctioning of the target compartment prior to implantation. These implanted isolation devices can be, for example, self-expanding occlusive stents that prevent air flow in both directions or one-way valves that allow flow in the exhalation direction only.

While a significant improvement over LVRS, ELVR can have a limited therapeutic benefit when the treated region in the lung is exposed to collateral ventilation from adjacent regions. The lungs comprise a plurality of compartments, referred to as lung compartments or lobes, which are separated from one another by a double layer of enfolded reflections of visceral pleura, referred to as fissures. While the fissures which separate the compartments are typically impermeable, in patients suffering from COPD, the fissures are frequently incomplete, leaving a pathway for collateral airflow or inter-lobular collateral ventilation. Such collateral airflow can result in the intrusion of air into the isolated lung compartments treated by ELVR, thus reducing or eliminating the desired volume reduction.

Collateral flow to diseased lung compartments can be detected, for example using the methods described in co-pending, commonly-owned U.S. patent application Ser. No. 11/296,591, filed on Dec. 7, 2005 (US 2006/0264772A1) and Ser. No. 11/550,660, filed on Oct. 18, 2006 (US 2007/0142742A1).

The catheter comprises a catheter body, and an expandable occluding member on the catheter body. The catheter body usually has a distal end, a proximal end, and at least one lumen extending from a location at or near the distal end to a location at or near the proximal end. At least a distal portion of the catheter body is adapted to be advanced into and through the airways of a lung so that the distal end can reach an airway which feeds a target lung compartment or segment to be assessed. The expandable occluding member, such as an inflatable balloon, is disposed near the distal end of the catheter body and is adapted to be expanded in the airway which feeds the target lung compartment or segment so that said compartment or segment can be isolated with access provided only through the lumen or catheter body when the occluding member is expanded. Simultaneously, the expandable occluding member may add to catheter function by centering the distal end of the catheter within the airway. In this state, inhaled air is precluded from entering the catheter lumen, while exhaled air from the isolated lung compartment can exit only through the catheter lumen.

The exhaled air exits the proximal end of the catheter lumen, which is coupled to an external console. The external console monitors the characteristics of the exhaled air, such as flow and pressure, and communicates the values associated with such characteristics to a user. If the flow and pressure decrease over time, a user may determine that the lung segment is not subject to collateral ventilation, and such segment is appropriately treated with ELVR.

While the use of these procedures can identify patients likely to benefit from ELVR procedures, the need for improvements exists, particularly during assessment in lung passageways containing bodily secretions, such as mucus. For instance, if mucus enters the catheter lumen, the air flow into the lumen will be impeded, thus interfering with the monitoring function of the external console and may lead to erroneous results. Further, in catheters utilizing an inflatable balloon, the balloon might distend due in some part to bubbles formed by mucus. This causes the catheter, to lean into the passageway, potentially blocking the opening. Further, when an obturator is used to introduce the catheter and is later withdrawn, the obturator may act as a syringe or piston and draw mucus into the catheter lumen.

For these reasons, it would be desirable to provide alternative and improved methods and apparatus for functional lung assessment within lung passageways containing secretions. In particular, it would be desirable to provide methods systems and devices that enhance catheter functionality by keeping secretions out of the catheter lumen, inhibiting secretion build-up within the passageways, cleaning secretions within the catheter lumen, or any combination thereof. At least some of these objectives will be met by the inventions described herein below.

SUMMARY OF THE INVENTION

In one aspect, the present application discloses devices, systems and methods for flushing or removing secretions or debris from a lumen of a catheter, such as a functional assessment catheter for the lungs. The pulmonary catheter is capable of being introduced transtracheally into an air passage of a lung segment. The pulmonary catheter comprises a distal end and a proximal end with a lumen disposed in-between.

In one aspect, the catheter may be modified to be connectable to a flushing unit that is connectable to a fluid source, wherein the flushing unit is configured to deliver a clearing fluid to the lumen of the pulmonary catheter to remove debris from the lumen. The flushing unit comprises a fixed volume fluid chamber connectable to the fluid source and a fluid restrictive element configured to regulate the delivery of the clearing fluid from the fluid chamber. The fluid chamber is configured to store a volume of the clearing fluid. The system may comprise a control unit configured to control a state of the fluid restrictive element In one aspect, the control unit is configured to transform the fluid restrictive element to a state whereby the fluid restrictive element allows the clearing fluid stored in the fluid chamber to be instantaneously released to flush the catheter.

In another aspect, the control unit is configured to transform the fluid restrictive element to a state whereby the fluid restrictive element allows a sustained release of the clearing fluid stored in the fluid chamber to flush the catheter over a period of time.

In yet another aspect, the flushing unit comprises two fluid restrictive elements, wherein the control unit is configured to control the first and second fluid restrictive elements. The control unit may be configured to transform the first fluid restrictive element to a state whereby the first fluid restrictive element allows the clearing fluid stored in the fluid chamber to be instantaneously released to flush the catheter, and to transform the second fluid restrictive element to a state whereby the second fluid restrictive element allows a sustained release of the clearing fluid stored in the fluid chamber to flush the catheter over a period of time.

Other aspects of the invention include methods corresponding to the devices and systems described above. One method for assessment of a lung compartment comprises the steps of providing a pulmonary diagnostic system comprising an endobronchial pulmonary diagnostic device connected a pulmonary catheter, said catheter having at least one measuring component connected with the device; introducing the distal end of the catheter to a compartment of a lung; generating measurement data characterizing the compartment of the lung with the pulmonary diagnostic system; and delivering a clearing gas from a flushing unit to flush the pulmonary catheter.

This and other aspects of the present disclosure are described herein.

BRIEF DESCRIPTION OF THE DRAWINGS

Present embodiments have other advantages and features which will be more readily apparent from the following detailed description and the appended claims, when taken in conjunction with the accompanying drawings, in which:

FIGS. 1a through 1d show exemplary embodiments of a catheter providing a component that diverts secretions away from the distal opening of the catheter.

FIG. 3 shows a catheter comprising an alternative embodiment that both attracts and collects the secretions away from the catheter opening.

FIGS. 4a and 4b show another exemplary embodiment providing an element that attracts the secretions away from the distal opening of the catheter.

FIGS. 5a and 5b show an alternative method of attracting secretions to a point distal to the catheter opening.

FIG. 9 shows another embodiment to attract the secretions to a site distal from the catheter tip.

FIG. 10 shows another embodiment to attract the secretions to a site distal from the catheter tip.

DETAILED DESCRIPTION OF THE INVENTION

Figure 1A:
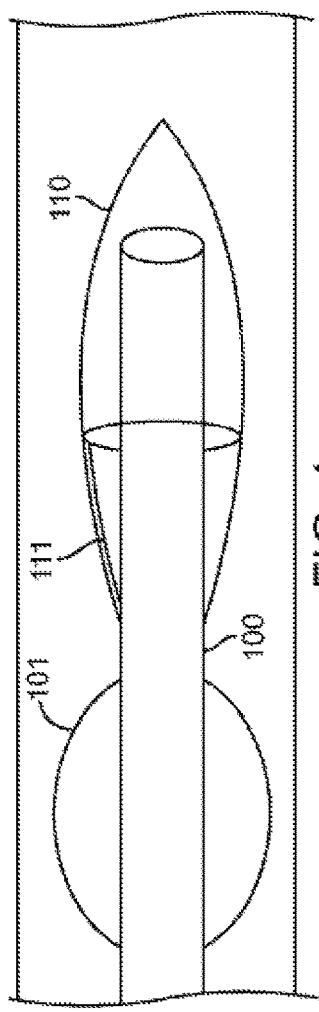

Although the detailed description contains many specifics, these should not be construed as limiting the scope of the disclosure but merely as illustrating different examples and aspects of the disclosure. It should be appreciated that the scope of the disclosure includes other embodiments not discussed herein. Various other modifications, changes and variations which will be apparent to those skilled in the art may be made in the arrangement, operation and details of the method, device, and system of the present embodiments disclosed herein without departing from the spirit and scope of the disclosure as described here.

Throughout the specification and claims, the following terms take the meanings explicitly associated herein unless the context clearly dictates otherwise. The meaning of "a", "an", and "the" include plural references. The meaning of "in" includes "in" and "on." Referring to the drawings, like numbers indicate like parts throughout the views. Additionally, a reference to the singular includes a reference to the plural unless otherwise stated or inconsistent with the disclosure herein.

The word "exemplary" is used herein to mean "serving as an example, instance, or illustration." Any implementation described herein as "exemplary" is not necessarily to be construed as advantageous over other implementations.

The present invention deals with methods systems and devices for preventing secretions from impeding the function of a pulmonary assessment catheter, hereinafter referred to simply as a catheter.

The various catheter embodiments described herein may be used singularly or in combination. In one aspect, secretions can be prevented from impeding the function of the catheter by preventing the secretions from entering the catheter lumen. Additionally or alternatively, secretions build-up in the airway could be prevented or inhibited. Additionally or alternatively, secretions that collect within the airway could be removed. Additionally or alternatively, the secretions could be repelled away from the distal tip of the catheter.

Figure 1B:
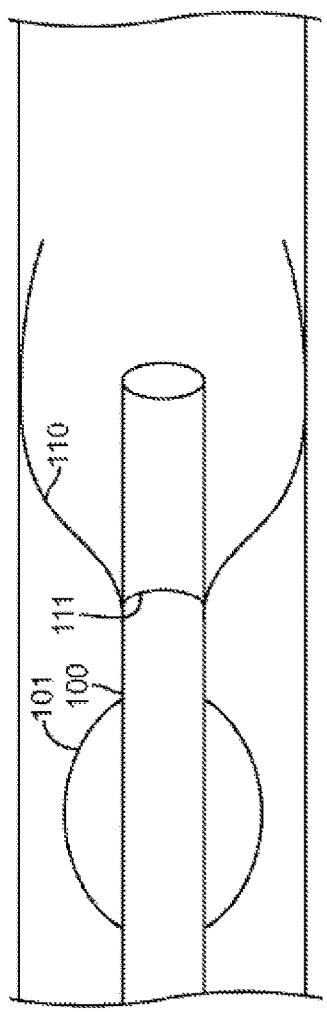

FIG. 1a shows an exemplary embodiment providing an expandable element that attracts the secretions away from the distal opening of a catheter 100 and precludes secretion entry into the catheter 100 during transport to the assessment site. Catheter 100 optionally comprises an expandable occluding member near its distal end, for example an inflatable balloon 101. A mesh 110 capable of forming a basket-like configuration is attached at a point proximal to the distal tip of the catheter 100, and distal to the balloon 101. The mesh 110 is composed of a biocompatible shape-memory material, for example nitinol. Optionally, the mesh 110 may comprise a coating, for example, silicone, at least on some portion thereof. In its initial configuration, the mesh 110 forms a cover for the distal opening of the catheter 100. The cover remains closed, as shown in FIG. 1a, while the catheter 100 is being transported to the assessment site. Secretions will thus be precluded from entering the lumen of the catheter 100 during such transportation. The proximal end of the mesh 110 is coupled to an elongate component 111, for example a wire or an obturator, configured to manipulate the mesh 110. Prior to deployment of the mesh 110, the elongate component 111 constrains the mesh 110 and prevents the mesh from expanding to its shape memory configuration. At the assessment site, the mesh 110 will be deployed by retracting the elongate component 111 and thereby releasing the mesh 110 from constraint to expand to its shape memory. Upon deployment, the mesh 110 obtains the configuration shown in cross section in FIG. 1b. In this configuration, the secretions would be caught within the outer diameter of the mesh 110, and would thus be diverted away from the distal tip of the lumen. Further, due to the surface tension of the secretions, the secretions would tend to pool within the mesh 110, and thus, secretion entry into the lumen would be delayed or eliminated. Simultaneously, the open configuration of the mesh 110 keeps the lumen of catheter 100 centered within the lung passageway, rather than leaning towards a wall within the lung passageway.

Figure 1C:
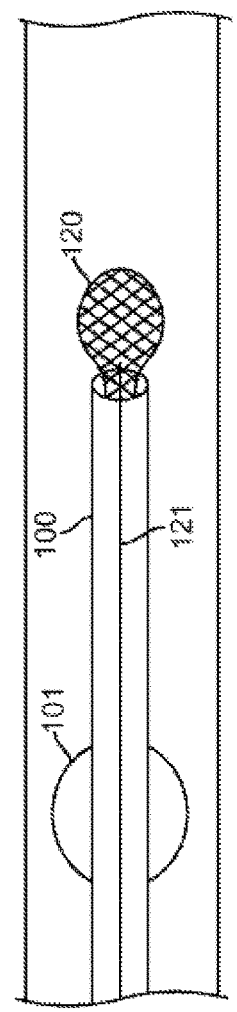

Alternatively or additionally, the mesh basket can be contained within the lumen of catheter 100, as shown in FIG. 1c. In this embodiment, the catheter 100 comprises a mesh 120 in a collapsed configuration within the distal tip of the catheter 100 until the catheter 100 is moved to the assessment site. Catheter 100 optionally also comprises a balloon 101. The mesh 120 is composed of a biocompatible shape-memory material, for example nitinol. Optionally, the mesh 110 may comprise an air-impermeable coating, for example, silicone, at least on some portion thereof. The proximal end of the mesh 120 is coupled to an elongate component 121, for example a wire or an obturator, configured to manipulate the mesh 120. The elongate component 121 maybe contained within the lumen wall of catheter 100 (as shown in FIG. 1c), or it may be contained anywhere within or on the catheter 100. Prior to assessment, the mesh 120 is deployed. The mesh 120 forms a ball-like structure of sufficient porosity to allow for air flow through the mesh 120. Simultaneously, the secretions would tend to adhere to the outer diameter of the mesh 120, and thus, secretion entry into the lumen of catheter 100 would be delayed or eliminated.

Alternatively, the mesh forms a funnel-like structure 130 that allows air to be directed into the catheter lumen as shown in FIG. 1d. In this embodiment, catheter 100 comprises a mesh 130 in a collapsed configuration within the distal tip of the catheter 100 until the catheter 100 is moved to the assessment site. The mesh 130 is composed of a biocompatible shape-memory material, for example nitinol. Optionally, the mesh 130 may comprise an air-impermeable coating 132, for example, silicone, at least on some portion thereof. The proximal end of the mesh 130 is coupled to an elongate component 131, for example a wire or an obturator, configured to manipulate the mesh 130. The elongate component 131 maybe contained within the lumen of catheter 100 (as shown in FIG. 1c), or it may be contained anywhere within or on the catheter 100. Prior to assessment, the mesh 130 is deployed to assume its shape memory of a funnel-like structure whose base is open to and engaged with the opening of catheter 100. In this embodiment, the mesh 130 acts to simultaneously preclude secretion entry into the catheter lumen while directing air within the passageway into the lumen of catheter 100. The secretions would tend to adhere to the outer diameter of the mesh 130, and thus, secretion entry into the lumen of catheter 100 would be delayed or eliminated. Simultaneously, when deployed, mesh 130 with coating 132 acts to seal the passageway and center the catheter 100 within the passageway such that the only outlet for air is through the funnel-like structure into the catheter lumen. Thus, in this embodiment, the mesh 130 may replace the balloon 101 shown in previous embodiments.

Figure 2A:
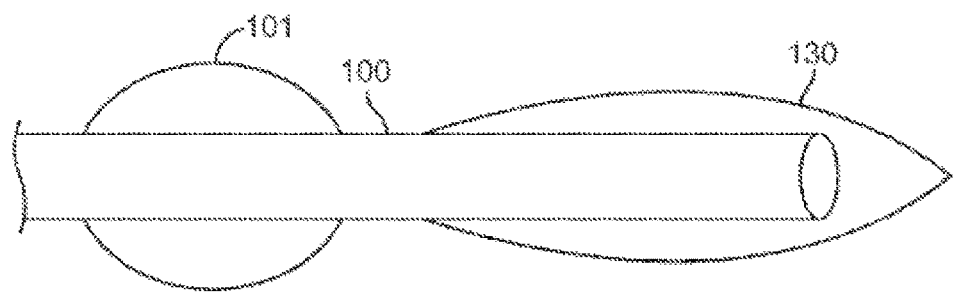
FIGS. 2a and 2b show a catheter comprising an element that could collect secretions away from the catheter opening.
Figure 2B:
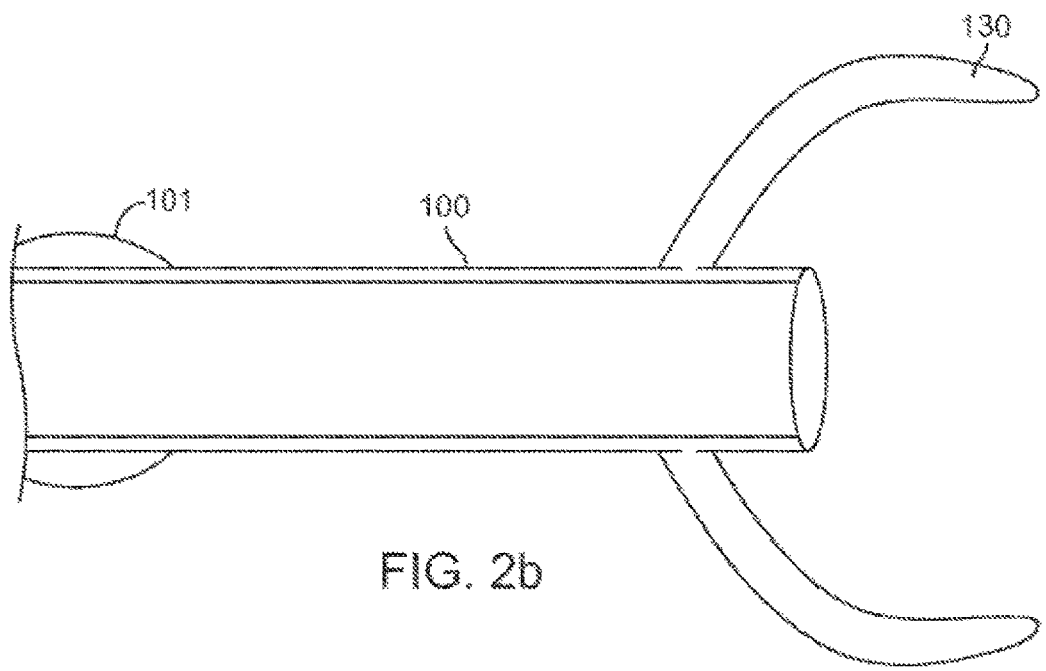

FIG. 2a shows an inflatable element 130 that could keep the secretions away from the opening of catheter 100. In one embodiment, the inflatable element 130 is located distal to the balloon 101 on the catheter 100. During transport, the distal tip of the inflatable element 130 is in an un-inflated state and covers the opening of the catheter 100 as shown in cross section in FIG. 2a. When inflated, the inflatable element 130 opens to reveal the lumen of catheter 100 as shown in cross section in FIG. 2b. Simultaneously, when the element 130 is inflated open, secretions that have thus far accumulated are pushed outwards and away from the lumen of catheter 100. Additionally, the inflatable element 130 keeps the distal tip of the catheter 100 centered within the lung passageway. Additionally or alternatively, the inflatable element 130 sealingly engages the lung passageway walls to perform the function of the balloon 101.

FIG. 3 shows an alternative embodiment to that shown in FIG. 2. This embodiment, shown in cross section, contemplates a collapsible rigid element 140, that is manipulated through elongate components such as a wire 141 contained within or on the catheter 100. The present figure shows the wire 141 contained within the wall of catheter 100. The wire 141 can be pulled back and forth by the user to open and close the rigid element 140. In this configuration, secretions will again pool along or behind the element 140, rather than into the lumen of catheter 100.

FIG. 4a shows, in cross section, another exemplary embodiment providing an element that attracts the secretions away from the distal opening of the catheter 100, and precluding secretion entry into the catheter 100 during transport to the assessment site. In this embodiment, the distal tip 200 comprises several strands 210 arranged to protrude radially from the distal tip 200. The distal tip 200 thus looks similar to a brush with several bristles. The strands 210 are composed of any suitable biocompatible material. The configuration of the strands 210 allows for air to flow into the lumen of catheter 100 during the assessment. Simultaneously, the secretions adhere to the strands 210 and away from the opening of the catheter 100. Optionally, the distal tip 200 of the catheter 100 also comprises several small apertures 211. The apertures 211 in the distal tip 200 of the catheter 100 facilitate air flow into the catheter 100. Optionally, the distal tip 200 could be manipulated within the passageway, for example in a backwards and forwards motion, to clean the area of assessment. Optionally, the strands 210 at the distal end may or may not be of a uniform length, and the strands 210 may form different cross sectional embodiments. Additionally, the distal section of the catheter 100 maybe detachably coupled or permanently affixed to the distal tip 200 of the catheter 100.

Additionally or alternatively, the strands 210 are connected to an elongate component contained within the catheter 100, for example a wire or obturator 212 as shown in FIG. 4b. It is transported as such to the assessment site. At the assessment site, the component 212 with the strands is deployed out of the catheter lumen and into the lung passageway. In one aspect, the component 212 with the strands may be held stationary at a point distal to the end of the catheter 100, to deflect the secretions. In another aspect, the component 212 with the strands may be moved along the lung passageway to clean the lung passageway and thereafter be held stationary at a point distal to the catheter 100, or be retracted through the lumen of catheter 100. Additionally, the strands 210 at the distal end may or may not be of a uniform length, and they may form different cross sectional embodiments.

FIGS. 5a and 5b show an alternative embodiment for attracting secretions to a point distal to the catheter opening. In this embodiment, tines 220 protrude longitudinally from the distal end of the catheter 100. The tines 220 could be made of any biocompatible material including nitinol, PTFE or silicone. During transport of catheter 100 to the assessment site, the tines 220 are held closed, for example using a ring 221 connected to a wire 222 contained within or on the catheter 100 as shown in FIG. 5a. At the assessment site, the tines 220 are opened, for example, by pulling on the wire 222 to retract the ring 221, as shown in FIG. 5b. The tines 220 keep secretions from entering the inner lumen of the catheter 100, by repelling the secretions if hydrophobic, or by preferentially attracting the secretions if hydrophilic.

In another embodiment of the present invention, a cover could be provided to prevent the secretions from entering the lumen of catheter 100, as shown in FIGS. 6a through 6d. The catheter 100 comprises a cover over the distal opening. Additionally, the catheter 100 comprises a wire 311 running the length of the lumen of catheter 100, from the proximal end accessible by a user, to a cover at the distal end. The wire 311 maybe soft or rigid. It may be contained within the lumen wall of catheter 100, or it may be contained anywhere within or on the catheter 100. The cover remains over the distal opening of the catheter 100 during the catheter's movement to the assessment site. Prior to or during assessment, the cover is opened or closed by manipulating the wire.

Figure 6A:
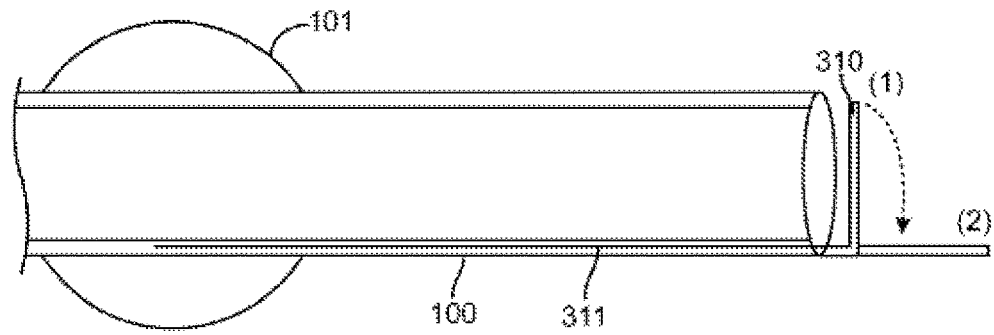
FIGS. 6a through 6d show a catheter embodiment comprising various covers.

For example, FIG. 6a shows a catheter 100 comprising a flap cover 310, wherein one end of said cover is manipulatable by the wire 311. In a closed position, the flap cover assumes the configuration as shown in position (1). When the wire 311 is pulled, the flap cover 310 is opened, as shown in position (2) to allow air to flow into the catheter 100 for assessment.

Figure 6B:
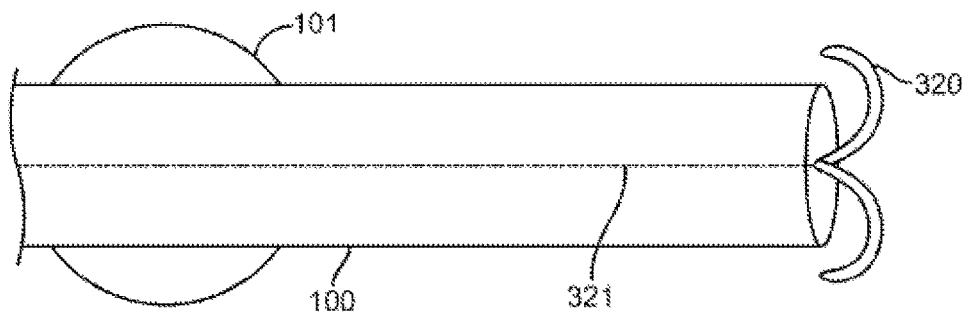

Another example is provided in FIG. 6b which shows a catheter 100 comprising a soft cover 320 that can be pushed forward or retracted by a wire 321. The soft cover 320 can be made of any flexible material, such as a plastic film, that will provide little or no suction when it is withdrawn through the lumen of catheter 100. During transport of the catheter 100, the soft cover 320 covers the distal opening of the catheter 100, thereby preventing or inhibiting secretion entry into the catheter 100. Prior to or contemporaneous with assessment, the soft cover 320 is manipulated via the wire 321, and the distal opening of the catheter 100 is open to receive air flow for assessment.

Figure 6C:
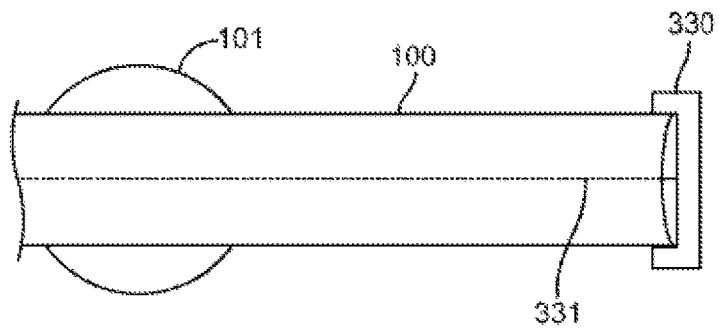

Alternatively, the cover may encapsulate the distal opening of the catheter 100, as shown in FIG. 6c. In this embodiment, the encapsulating cover 330 may encase the opening of the catheter 100. The encapsulating cover 330 is attached to the wire 331 and can be pushed out into the lung passageway for the assessment procedure.

Figure 6D:
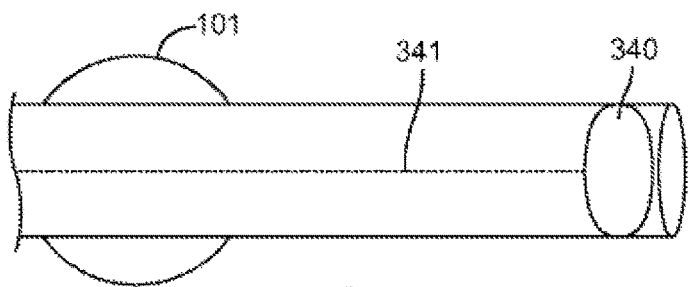

In another embodiment, the cover may be a balloon 340 within the lumen of the catheter 100 as shown in FIG. 6d. The balloon 340 is attached to an elongate component, such as a wire 341, of a small enough diameter to not act as a syringe when being pulled out. When inflated, the balloon 340 prevents secretion entry into the lumen of catheter 100. During assessment, it may be deflated and pulled back with the wire 341 to leave an open catheter lumen.

Figure 7:
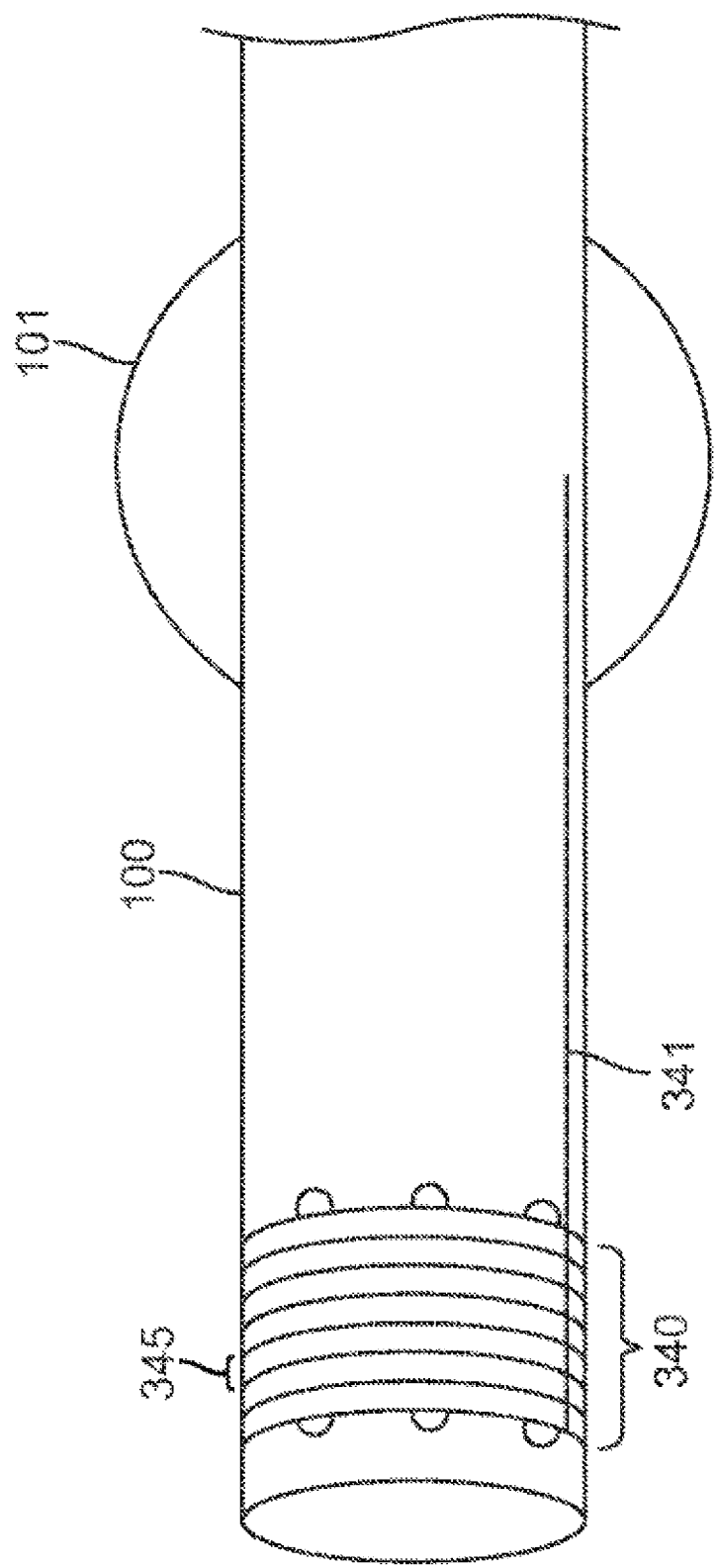
FIG. 7 shows a cover for the distal tip that is incrementally removable.

FIG. 7 shows a cover for the distal tip of the catheter 100 that is incrementally removable. The distal tip of the catheter 100 comprises a layered cover 340 with removable layers 345 made of a biocompatible material. The distal tip of the catheter 100 may or may not be perforated. The layers 345 are incrementally removable through one or more attachments, such as a wire 341 contained within the layers that extends the length of the catheter 100 to the user. Additionally, the biocompatible material may or may not be hydrophilic. In one embodiment, the distal tip of the catheter 100 may be transported to the assessment site, where the layers 345 are removed. In another embodiment, the layers 345 may be removed incrementally during the assessment process. For example, in the embodiment with apertures in the catheter 100, if secretions were to impede the air flow into the catheter 100, several of the layers 345 could be removed to expose another set of apertures in the catheter 100.

Figure 8:
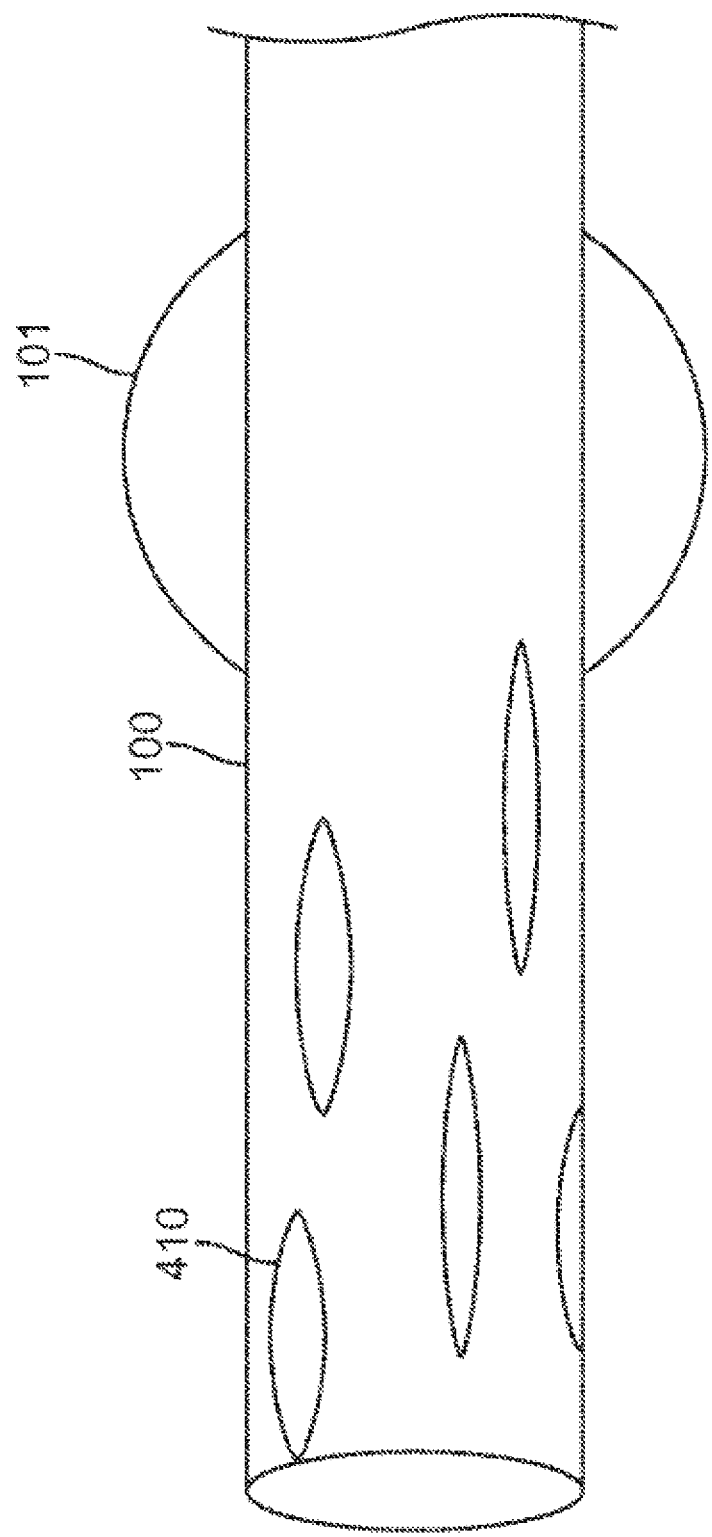
FIG. 8 contemplates methods for enhancing assessment even when the distal opening of the catheter is not centered within the lung passageway.

FIG. 8 contemplates methods for enhancing assessment even when the distal opening of the catheter 100 is not centered within the lung passageway, for example, through distension of the inflatable balloon 101. In this embodiment, the catheter 100 comprises apertures 410 within the catheter wall at the distal end. The apertures 410 may be of any size or shape and may be organized in any pattern while maintaining catheter 100 integrity. For example, the apertures 410 are elongate to allow the catheter 100 to maintain structural rigidity. The apertures 410 are scattered throughout the circumference of the catheter 100, so that even if some of the openings of the catheter 100 are plugged with secretions, other openings will remain clear. Additionally, even if one portion of the catheter 100 leans against the lung passageway wall, the opposite portion will have some of the apertures 410 exposed to the gases contained within the lung passageway. Thus, the assessment function of the catheter 100 will not be impaired.

FIG. 9 shows another embodiment to attract the secretions to a site distal from the tip of the catheter 100. In this embodiment, an elongate coil 510 is deployed from the distal tip of the catheter 100. The elongate coil 510 can be made of any biocompatible shape memory material, for example, nitinol. While transporting catheter 100 to the assessment site, the elongate coil 510 is contained within the lumen wall of catheter 100 in a straight-line configuration, such as a wire 511. The wire 511 is then pushed out of the distal opening and coils to assume the configuration of the elongate coil 510 within the lung passageway. Alternatively, the elongate coil 510 could be contained in a compressed, but coiled state within the lumen wall of the catheter 100 while transporting to the assessment site. The elongate coil 510 could then be deployed into the lung passageway, where it would expand into the lumen wall. The secretions along the wall passageways would adhere to the points of the elongate coil 510 in contact with the lung passageway wall rather than to the catheter 100. Simultaneously, the inner diameter of the elongate coil 510 is open and allows enough air to flow into the assessment catheter 100. In another embodiment, the elongate coil 510 would cover a portion of the distal end of the catheter 100.

FIG. 10 shows another embodiment to attract the secretions to a site distal from the tip of the catheter 100. In this embodiment, a flat coil 520 is deployed from the distal tip of the catheter 100. The coil can be made of any biocompatible memory-shape material, for example, nitinol. During catheter transport to the assessment site, the coil is contained within the lumen wall of catheter 100 in a straight-line configuration such as a wire 521. The wire 521 is then pushed out of the distal surface and assumes the shape of a flat coil 520 within the lung passageway. The flat coil 520 is then deployed into the lung passageway, where it would expand to the diameter of the lung passageway. The secretions along the lung passageway walls would adhere to the points of the flat coil 520 in contact with the lung passageway wall. Simultaneously, the inner diameter of the flat coil 520 would be sufficiently open to allow for enough air flow into the assessment catheter 100.

Figure 11:
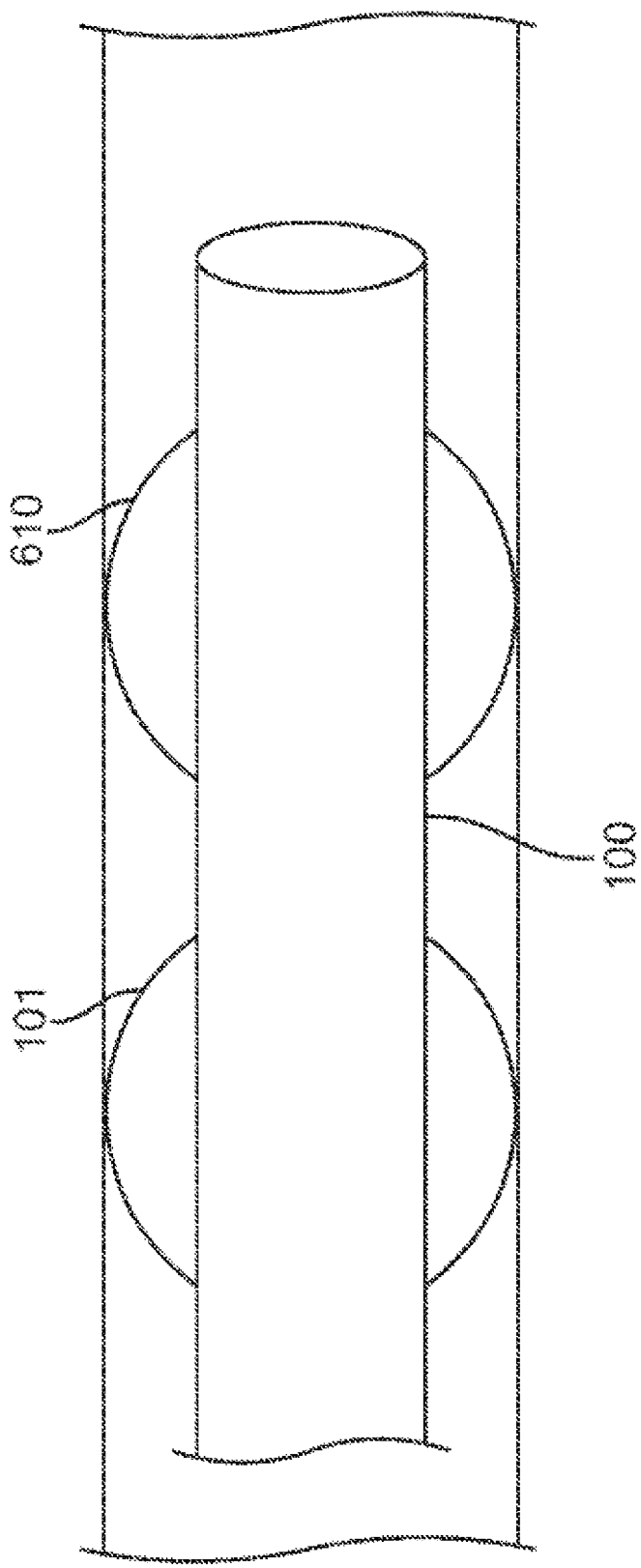
FIG. 11 shows an alternative method of preferentially attracting the secretions to a site away from the inner lumen of the catheter.

FIG. 11 shows an alternative method of preferentially attracting the secretions to a site away from the inner lumen of the catheter 100. The distal tip of the catheter 100 comprises an addition, for example, a coating or a pad or a paper cone, of an absorbent material 610. The absorbent material 610 can comprise any biocompatible, absorbent material, and may or may not be expandable. The coating of absorbent material 610 may end proximal to the distal tip of the lumen during assessment. Secretions at the assessment site will thus be absorbed by the absorbent material. As some secretions are absorbed by the absorbent material 610, it cohesively attracts more secretions. Thus, secretions that thereafter reach the assessment site will be attracted to the absorbent material, 610 rather than to the wall of catheter 100.

Figure 12:
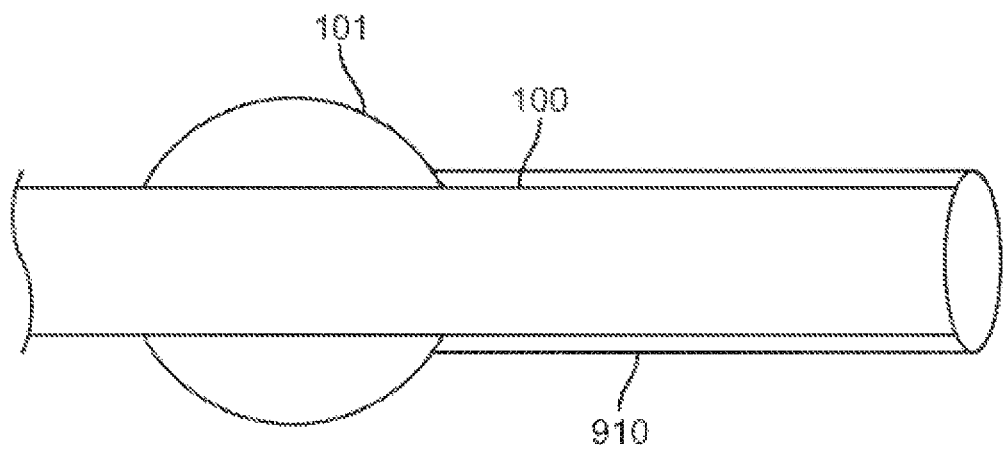
FIG. 12 contemplates a method for cleaning the inner lumen of the catheter once secretions have actually entered the catheter.

FIG. 12 shows an alternative method of repelling the secretions by modifying the distal tip of the catheter 100. Traditionally, catheters are coated with PEBAX, which adheres to secretions. The present embodiment contemplates coating the distal tip with a hydrophobic substance 910, for example PTFE, to divert secretions away from the lumen of catheter 100.

Figure 13:
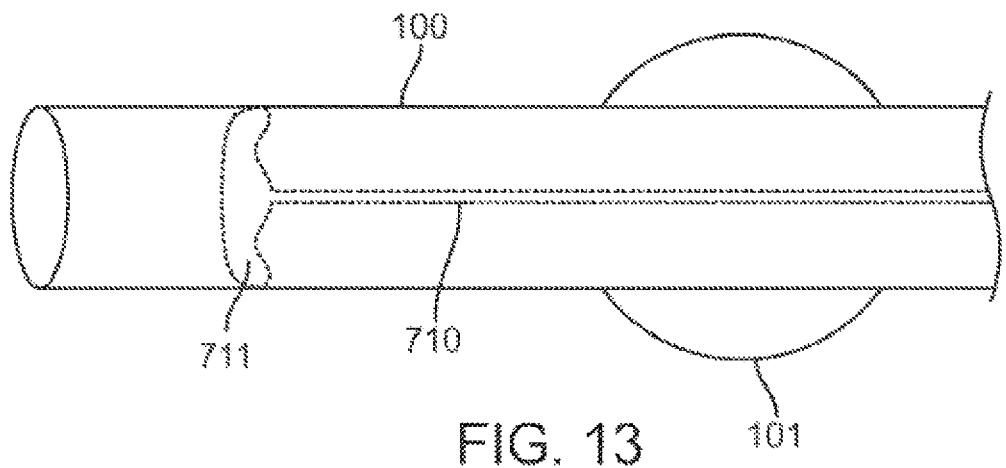
FIG. 13 shows an alternative method of repelling the secretions by modifying the distal tip of the catheter.

FIG. 13 contemplates a method for cleaning the inner lumen of the catheter 100 once secretions have actually entered the catheter 100. In this embodiment, the inner lumen of the catheter 100 comprises an elongate inner component, such as a wire 710, extending from the proximal end to the distal end, terminating at the distal end in a radial element 711. The radial element 711, shown in cross section in FIG. 13, has an outer diameter that is substantially similar to or slightly less than the inner diameter of the catheter 100. If secretions enters the inner lumen of the catheter 100, the radial element 711 is moved in a distal direction and past an amount of secretions that is to be removed, and subsequently back in a proximal direction, thereby moving the secretions contained within the lumen in a proximal direction, and optionally removing the secretions from the proximal end of the catheter 100. Alternatively, the radial element 711 is moved in a distal direction to push secretions contained within the lumen in a distal direction.

Another embodiment of the present invention contemplates alternative obturators. In this embodiment, the obturator has a different shape to simultaneously keep enough secretions out while at the same time exerting little or no negative pressure at the distal end of the catheter, thereby allowing the obturator to retract without drawing secretions. For example, the cross section of the obturator could be flower shaped, star shaped or cross shaped. Additionally or alternatively, the obturator could be hollow. A hollow obturator may additionally be used as an aspiration port to aspirate the lung passageway during transport, assessment, or any combination thereof.

Additionally or alternatively, the obturator is configured to act like an Archimedes screw. Whenever the distal opening of the catheter 100 encounters secretions, the screw-shaped obturator will channel the secretions through the catheter 100 and away from the site of the assessment.

In another embodiment of the present invention, one or more elements could be stored within or on the distal tip of the catheter to dry or otherwise preclude secretion build-up within the catheter. For example, a heating element may be used to dry the airway. Alternatively, medications that minimize mucus formation (e.g., a mucolytic drug) may be coated on the catheter tip. The drug can diffuse slowly out of the coating into the surrounding tissue and provide extended release of a drug that can prevent or minimize mucus formation or breakdown the mucus that is secreted by the local tissue.

In another embodiment of the present invention, at least one extra lumen and corresponding port may be provided to aspirate the passageways, dry the passageways, flush the passageways, aerate the passageways, introduce a mucolytic drug into the passageways or any combination thereof. Alternatively, aspiration could occur via the existing lumens and ports. This is facilitated via a modified proximal portion of the catheter that is configured to introduce a fluid, (e.g., air) into the catheter. The introduced fluid would emerge from the distal end of the catheter with sufficient force to dry (if air or another gas is used) or push secretions that accumulate near or around the catheter mouth.

Figure 14:
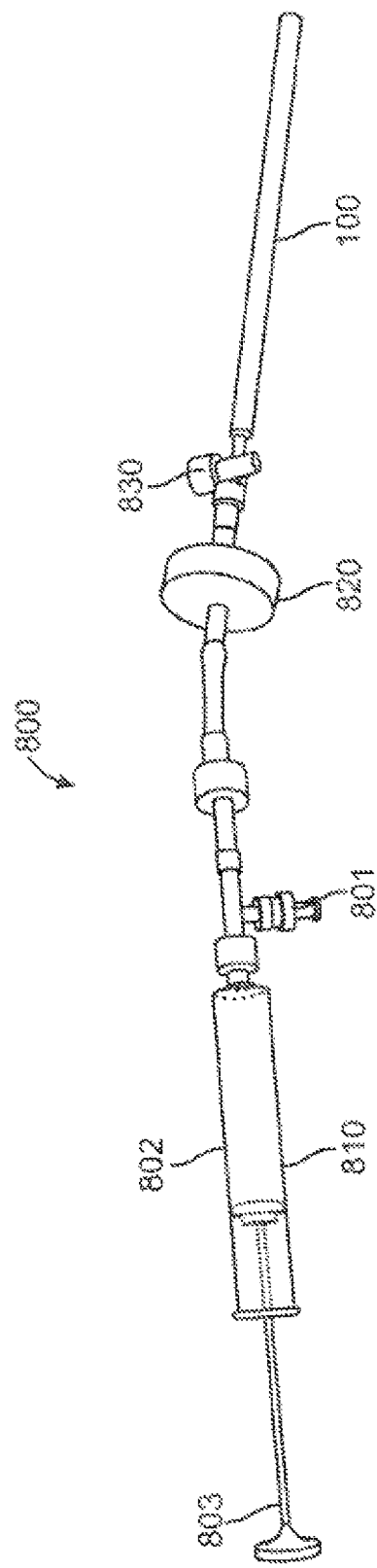
FIG. 14 shows a catheter attached to a syringe.

An example of such a modified proximal portion is shown in FIG. 14. In this embodiment, the proximal portion of the device is configured to receive a fluid-propelling mechanism 800. The fluid-propelling mechanism 800, such as a syringe, comprises a propellant portion 810 at the proximal end of the device, and a release valve 830 at the distal end of the device, and a pressurizer 820 therebetween. The propellant portion 810 further comprises an intake port 801, a chamber 802 and a plunger 803. A fluid is introduced into intake port 801 and is drawn into the chamber 802 in a syringe-like manner by pulling on plunger 803. Intake port 801 is configured to be one-way or closeable to preclude fluid from exiting intake port 801 from chamber 802. Thereafter, the plunger 803 is pushed into chamber 802 to direct fluid into the pressurizer 820. The fluid is precluded from exiting the distal end of mechanism 800 by release valve 830, which remains in a closed position in a default state. Simultaneously, the fluid is held under pressure in the pressurizer 820. When secretions are to be removed, release valve 830 is opened. The fluid, which has been accumulated under pressure in the pressurizer 820, will exit the mechanism 800 and enter the catheter 100. The fluid will have sufficient force that upon exiting the distal end of catheter 100, it will dry or move secretions accumulating around the catheter end.

In another embodiment, a catheter 100 is configured to maintain structural rigidity during transport without the use of an obturator. In another embodiment, the tip of catheter 100 is configured to be angular to enhance air flow into the catheter lumen. In another embodiment, the balloon 101 is inflated with a fluid, such as saline, to provide added stability. This will aid the catheter 100 to be centrally maintained within the lung passageway. Alternatively, the balloon 101 is manufactured to be structurally symmetrical when inflated.

Figure 15A:
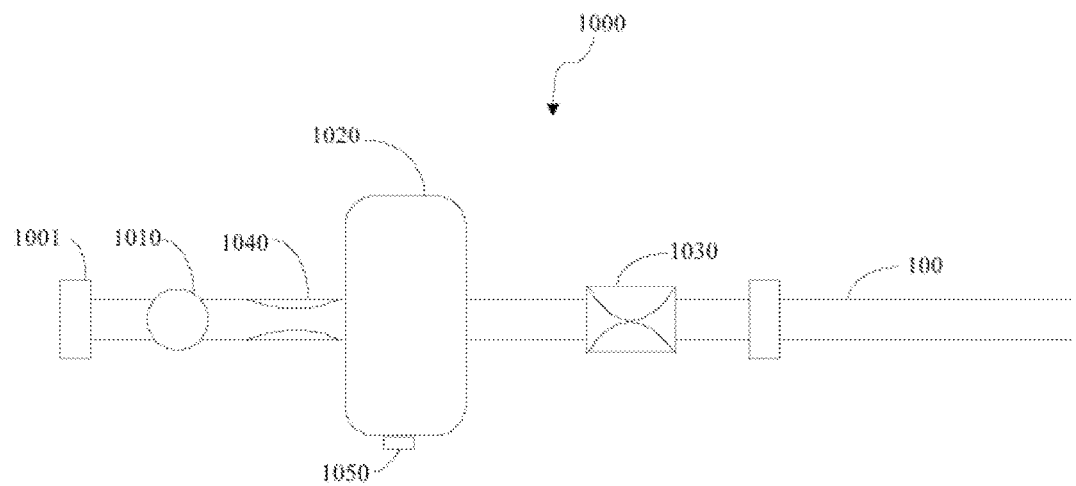
FIGS. 15a-15b show a catheter attached to flushing mechanisms.
Figure 15B:
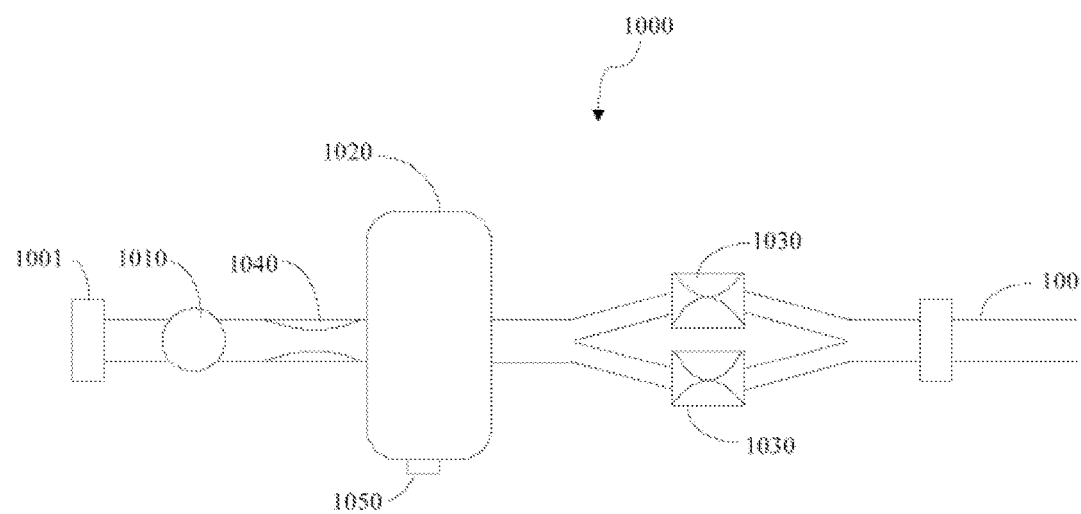

Another embodiment of the present disclosure is shown in FIGS. 15a-15b. In this embodiment, the proximal portion of the catheter 100 is configured to be connectable to a flushing element 1000. The flushing element 1000 is configured to deliver a clearing fluid to the lumen of the catheter 100 to remove debris, secretions, or moisture from the lumen or sensors. In one embodiment the flushing element 1000 is configured to be connectable to the proximal end of the catheter 100. The flushing element 1000 may alternatively be integrated into the proximal end of the catheter 100.

In one embodiment, the distal end of the flushing element 1000 comprises one or more intake ports 1001 configured to connect the flushing element 1000 to a fluid source such as a pump, a pressurized gas chamber, a wall oxygen unit, or any other fluid source. In one embodiment the flushing element 1000 is configured to be connectable to multiple fluid sources simultaneously. In one embodiment, the intake port 1001 is configured to be one-way or closeable to preclude fluid from exiting the intake port 1001. The flushing element 1000 comprises a pressure regulator 1010 distal to the intake port 1001 configured to regulate the pressure and flow of fluid from the fluid source into the flushing element 1000. The flushing element 1000 further comprises a release valve 1030 at the distal end of the device and a pressurizer 1020 between intake port 1001 and release valve 1030. The pressurizer 1020 is a rigid chamber of fixed volume configured to store the clearing fluid and act as a flush capacitor. Pressurizer 1020 may comprise a variable release safety valve 1050 configured to allow the release of pressure from the system. In one embodiment a flow restrictive element 1040 is located between the pressure regulator 1010 and the pressurizer 1020. The clearing fluid may be any biocompatible fluid including oxygen, nitrogen, carbon dioxide, or any other biocompatible fluid.

In one embodiment, fluid is precluded from exiting the distal end of flushing element 1000 by release valve 1030, which remains in a closed position in a default state. Simultaneously, the fluid is held under pressure in the pressurizer 1020. When secretions are to be removed, release valve 1030 is opened. The fluid, which has been accumulated under pressure in the pressurizer 1020, will exit the flushing element 1000 and enter the catheter 100. The fluid will have sufficient force that upon exiting the distal end of catheter 100, it will dry or move secretions accumulating around the catheter end.

In another embodiment, the release valve 1030 is a flow restrictive element controlled by a control unit. Control unit is configured to open and close the release valve 1030. Release valve 1030 may be a solenoid valve wherein the control unit comprises a solenoid. In one embodiment the control unit is configured to transform release valve 1030 to a state whereby the release valve 1030 allows the clearing fluid stored in the pressurizer 1020 to be instantaneously released to flush the catheter 100 (not shown). In another embodiment, the control unit is configured to transform release valve 1030 to a state whereby the release valve 1030 allows a sustained or continuous release of the clearing fluid stored in the pressurizer 1020 to flush the catheter 100 over a period of time to prevent secretion or debris buildup.

In one embodiment, the flushing element 1000 may comprise multiple release valves 1030 connected in parallel. In one embodiment flushing element 1000 comprises an instantaneous release valve and a sustained release valve. If multiple release valves are present, a single control unit may separately control all release valves 1030. Alternatively, each release valve 1030 may be controlled by separate control units. Release valve 1030 may be configured to have a closed state, an open instantaneous release state, and a partially open sustained release state, wherein the control unit is configured to transform the release valve 1030 to allow instantaneous or sustained release of fluid. For example, in one embodiment, the instantaneous release of fluid and the sustained release of fluid may be performed in tandem, where one release valve maintains a partially open sustained release state to continuously release the fluid to prevent or minimize secretion or debris buildup, contemporaneously, the operator may instantaneously release the fluid to further flush the catheter 100. Alternatively, the instantaneous flushing and sustained flushing may be performed in sequence.

In another embodiment, the release valve 1030 may be variably opened to allow adjustable release of fluid. Control unit may further be configured to control pressure regulator 1010, safety valve 1050, flow restrictive element 1040, or the selection of fluid source.

Any or all of the above embodiments may be combined or replaced with medication prior to the assessment procedure.

While the above is a complete description of various embodiments, any of a number of alternatives, modifications, and equivalents may be used in alternative embodiments. Therefore, the above description should not be taken as limiting the scope of the invention as it is defined by the appended claims.

What is claimed is:

1. A pulmonary diagnostic system, comprising:
a pulmonary catheter configured to be introduced transtracheally into a lung passageway of a lung segment in a patient, wherein the pulmonary catheter comprises a distal end and a proximal end with a lumen disposed in-between; and
a flushing unit comprising:
an intake port connectable to a gas source;
a pressure regulator distal to the intake port configured to regulate the pressure and flow of a clearing gas from the gas source into the flushing unit;
a first gas restrictive element;
a fixed volume gas chamber between the intake port and the first gas restrictive element, wherein the gas chamber is configured to store a volume of the clearing gas and act as a flush capacitor, and wherein the first gas restrictive element is configured to regulate delivery of the clearing gas from the gas chamber; and a control unit configured to control a state of the first gas restrictive element;

wherein the flushing unit is configured to deliver the clearing gas to the lumen of the pulmonary catheter and out the distal end into the lung passageway with sufficient force to remove debris from the lumen while the distal end is within the lung passageway of the lung segment in the patient.

2. The system of claim 1, wherein the control unit is configured to transform the first gas restrictive element to a state whereby the first gas restrictive element allows the clearing gas stored in the gas chamber to be instantaneously released to flush the catheter.

3. The system of claim 1, wherein the control unit is configured to transform the first gas restrictive element to a state whereby the first gas restrictive element allows a sustained release of the clearing gas stored in the gas chamber to flush the catheter over a period of time.

4. The system of claim 1, wherein the flushing unit further comprises:

a second gas restrictive element configured to regulate the delivery of the clearing gas from the gas chamber;

wherein the control unit is configured to control a state of the second gas restrictive element, wherein the control unit is configured to transform the first gas restrictive element to a state whereby the first gas restrictive element allows the clearing gas stored in the gas chamber to be instantaneously released to flush the catheter, and wherein the control unit is configured to transform the second gas restrictive element to a state whereby the second gas restrictive element allows a sustained release of the clearing gas stored in the gas chamber to flush the catheter over a period of time.

5. The system of claim 1, further comprising a sensor connectable to the catheter, wherein the clearing gas delivered by the flushing unit is configured to clear the debris from the sensor.

6. The system of claim 1, wherein the gas chamber comprises a safety valve.

7. The system of claim 1, wherein the flushing unit is configured to deliver the clearing gas to the lumen of the pulmonary catheter and out the distal end into the lung passageway with sufficient force to dry the lumen while the distal end is within the lung passageway.

8. The system of claim 1, wherein the flushing unit is configured to deliver the clearing gas to the lumen of the pulmonary catheter and out the distal end into the lung passageway without introducing a cleaning liquid into the lung passageway.

9. The system of claim 1, wherein the system is a basin-free system.

10. The system of claim 1, wherein the flushing unit further comprises a flow restrictive element located between the pressure regulator and the gas chamber.

* * * * *